United States Patent [19]
Russell, Jr.

[11] 3,947,701
[45] Mar. 30, 1976

[54] DIGITALLY CONTROLLED VARIABLE IMPEDANCE FOR CURRENT NORMALIZATION IN AN ELECTROLYTE TYPE PARTICLE SENSING ZONE

[75] Inventor: Dennis Russell, Jr., Downers Grove, Ill.

[73] Assignee: Particle Data, Inc., Elmhurst, Ill.

[22] Filed: Jan. 13, 1975

[21] Appl. No.: 540,557

Related U.S. Application Data

[63] Continuation of Ser. No. 380,369, July 18, 1973, abandoned.

[52] U.S. Cl. .......... 307/264; 307/235 T; 324/57 PS; 324/63; 324/71 CP; 343/17.7
[51] Int. Cl.² .................... H03K 1/14; G01N 27/00
[58] Field of Search ..... 307/264, 235 T; 324/57 PS, 324/63, 71 CP; 343/17.7; 330/86

[56] References Cited
UNITED STATES PATENTS 3,345,502  10/1967  Berg et al. ................. 324/71 CP
3,629,720  12/1971  Sedra et al. ..................... 330/86
3,745,455  7/1973  Haigh ........................ 324/71 CP Primary Examiner—Stanley D. Miller, Jr.
Attorney, Agent, or Firm—Hill, Gross, Simpson, Van Santen, Steadman, Chiara & Simpson

[57] ABSTRACT

A digitally controlled variable impedance, preferably for use in a current normalizer for particle analysis apparatus, includes a variable resistance connected to a counting register by a plurality of opto-isolators in the form of light emitting diode-light responsive transistor combinations. The register is reset (or preset) to a predetermined count and operates to change the impedance value in response to receipt of each pulse of a pulse train. A circuit is provided to terminate counting in response to an interpulse interval of greater than a predetermined interval to indicate a null condition between pulse amplitude, the pulses traversing the impedance, and a reference amplitude.

6 Claims, 2 Drawing Figures

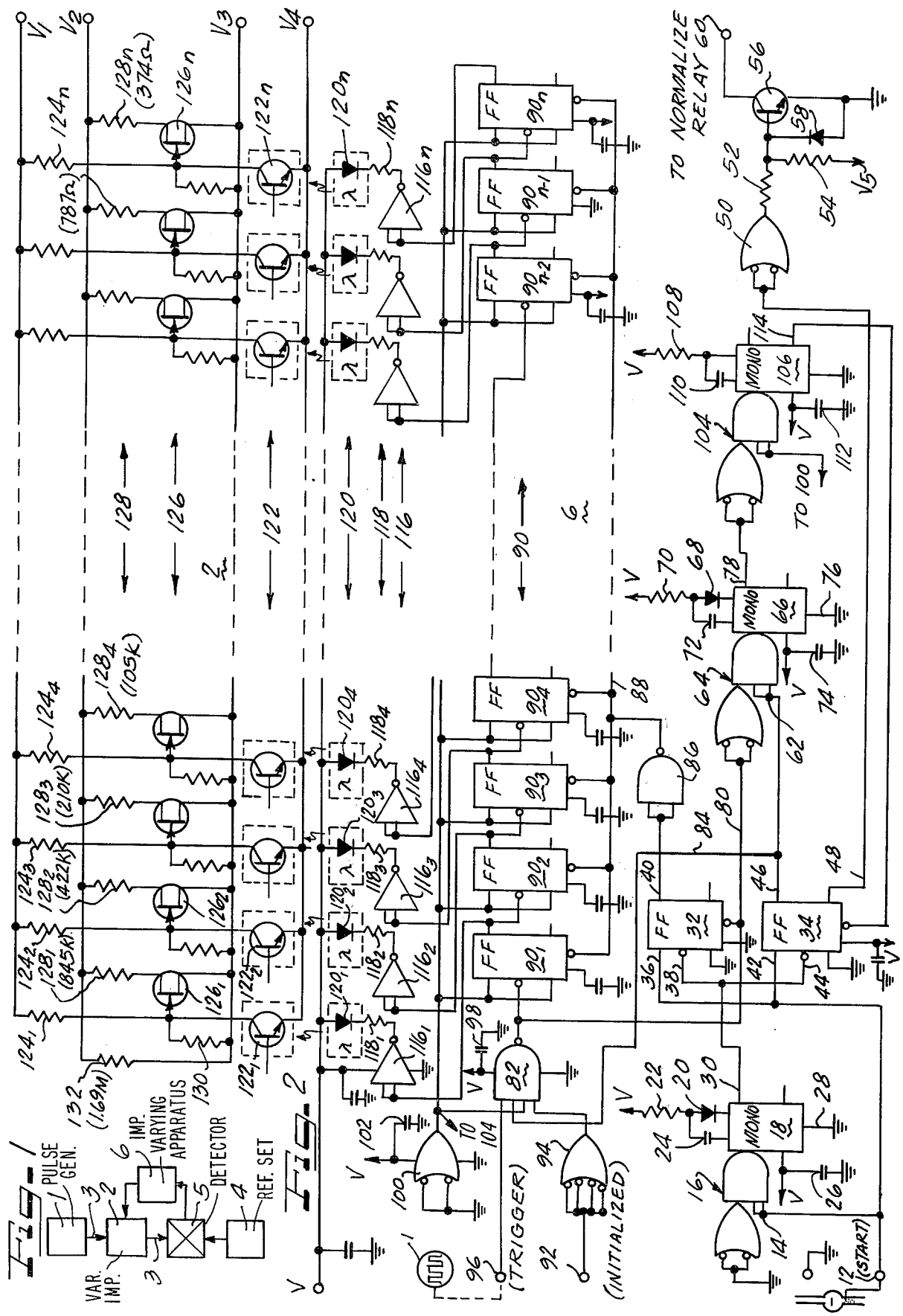

DIGITALLY CONTROLLED VARIABLE IMPEDANCE FOR CURRENT NORMALIZATION IN AN ELECTROLYTE TYPE PARTICLE SENSING ZONE

This is a continuation of application Ser. No. 380,369, filed July 18, 1973, now abandoned.

BACKGROUND OF THE INVENTION

1. Field of the Invention

This invention relates to a current normalizer, and in particular to a current normalizer having a digitally controlled variable impedance for automatically effecting current normalization in measuring the resistance of an electrolyte type particle sensing zone.

2. Description of the Prior Art

Sensing zones for particle analysis apparatus are constructed in various configurations, one of the most widely used being of the type disclosed in U.S. Pat. No. 3,345,502 of Robert H. Berg. This type of sensing zone comprises a beaker having an electrolyte containing suspended particles therein and an orifice tube containing electrolyte emersed in the electrolyte of the beaker. One terminal from a current source is positioned within the orifice tube and the other terminal of the current source is positioned within the beaker whereby modulations of the developed voltage across the orifice in the form of particle pulses may be sensed as a sample of suspended particles to be analyzed is caused to flow through the orifice. As noted by Geoffrey T. Haigh in his U.S. Pat. No. 3,745,455, issued July 10, 1973, and as the present invention, assigned to Particle Data, Inc., when a particle traverses a given orifice, there will be a change in the resistance of the orifice proportional to the product of the volume of the particle and the resistivity of the electrolyte. For an orifice which measures 10,000 ohms, for example, a 10-ohm change for a particle entering a given orifice might be obtained. If the resistivity of the electrolyte is changed such that the orifice resistance is 20,000 ohms, a 20-ohm change will occur for the same particle. However, when a current is forced through the electrolyte, some degree of back voltage is generated due to polarization at the electrodes.

Haigh observed that if the current through the electrode is held constant, the momentary current change caused by passage of a particle is independent of electrolyte resistivity, and that if the voltage drop across the orifice alone is held constant, the current change caused by passage of the particle is independent of electrolyte conductivity. He further observed that holding the voltage constant is not practicable; whereas, holding current constant may be practically realized. This results because, when the amplifier input impedance is nearly matched to that of the orifice, as is generally desirable for the best signal to noise ratio, the amplifier is sensing partly voltage change and partly current change at the orifice. Therefore, the sensed signal is proportional to the volume of the particle and some fractional power of the resistivity of the electrolyte. Correspondingly, the provision of a voltage source to program the orifice is insufficient because the counter-emf generated by electrode polarization is a variable.

In view of the above, Haigh provided current programming of the orifice so that a constant voltage drop is provided across the resistance of the orifice. As an implementation, the resistance of the orifice for a given electrolyte is measured and the system is adjusted to compensate for that resistance. The details of the implementation may be had by reference to the aforementioned Haigh patent which is fully incorporated herein by this reference. It should be pointed out, however, that the current programming is effected in that disclosure by means of a potentiometer or the like while utilizing the instrument operator for visually observing a scope and/or pulse count rate indicator from which to manually adjust the supply current.

SUMMARY OF THE INVENTION

It is highly desirable and the primary object of the present invention to automatically normalize current during measurement of the resistive element of the orifice.

Inasmuch as the present invention may be advantageously utilized in systems other than those used for particle analysis, another object of the invention is to provide apparatus for automatically varying an impedance to obtain a null between a signal developed at the impedance and a reference signal.

Another object of the invention is to achieve a reproducible null point by removing human judgment from the system control in addition to the usual advantages in replacing the human element in monitoring and control situations and freeing a human operator from a degree of tedium.

According to the invention, an impedance comprising a plurality of weighted value resistors is connected in circuit with a current source whose output is to be normalized and employed as a standard. The individual resistors of the impedance are electrically isolated from and coupled to a counting register by means of a like plurality of light emitting diode isolators which effect the conductivity of respective transistors to control the switching in and out of the resistors by way of respective field effect transistors (FET).

The counting register is clocked in response to trigger pulses from a comparator which receives the trigger pulses and a reference level. Apparatus in the form of monostable and bistable circuits control the operation and reset of the register and monitor the presence of trigger pulses to control connection and disconnection of the current normalizer and the orifice. According to the invention, therefore, the impedance and its control circuits may therefore generally replace the manually operated normalizing components such as the elements 22, 16-5, etc of the aforementioned prior art circuit of Haigh, and may readily be completely integrated with the remainder of that circuit as will be apparent from the following detailed description of a preferred embodiment of the invention.

A primary advantage of the present invention is that entirely digital means are employed in controlling current adjustment to provide all of the well known advantages of digital circuitry, among those principally including the absence of sensitivity to drift factors which are a persistent problem in analog circuits of almost every known kind.

BRIEF DESCRIPTION OF THE DRAWING

Other objects, features and advantages of the invention its organization, construction and operation will be best understood from the following detailed description of a preferred embodiment thereof taken in conjunction with the accompanying drawing, on which:

FIG. 1 is a block diagram of a current normalizer; and

FIG. 2 is a schematic circuit diagram of a digitally controlled variable impedance constructed in accordance with the principles of the present invention.

DESCRIPTION OF THE PREFERRED EMBODIMENT

Referring first to FIG. 1, a block diagram is illustrated for a current normalizer which comprises a generator 1 which produces a train of electrical pulses of constant amplitude, a variable impedance 2, apparatus 3 for passing the pulse train through the impedance in such a manner that variance in the impedance effects variance in the pulse train amplitude at a detecting point, means 4 for setting a reference amplitude at the detecting point, a detector 5 for determining whether and when the pulse train amplitude is matched to the reference amplitude, and a means 6 for varying the impedance in response to signals from a detector 5. The elements 1–5 are fully disclosed in the aforementioned Berg and Haigh patents. These disclosures are fully incorporated herein by reference and will not be dealt with in detail; however, it should be pointed out that element 6 is constituted in the Haigh disclosure by a human operator who observes the detector 5, for example a scope, and manually manipulates the impedance 2, an ordinary potentiometer.

The present invention recognizes, first of all, that an off-null signal at the detector 5 is inherently digital, and secondly that a digital representation of an off-null condition can be transformed to a useful analog control. This analog control could be employed for driving a servomotor or the like to operate a multi-turn potentiometer in place of the manually manipulated potentiometer of the Haigh circuit. However, the off-null condition as represented by a digital signal may most advantageously be utilized on an entirely digital basis with a transformation to a useful analog presentation at the point of utilization.

The aforementioned approach, as noted above, provides all of the well known advantages of digital circuitry, principally the absence of sensitivity to drift factors.

In the particular embodiment disclosed herein, the purpose of the invention is to inject a current pulse through the impedance 2 in order to achieve a ready means for electrolyte conductivity compensation.

It will be appreciated that inasmuch as the present invention digitally controls the impedance 2, there must be some inherent unit impedance change corresponding to how finally divided the digital incrementing is effected. In the particular embodiment disclosed herein, the circuit was designed for 4096 such increments over the full range of variance of the impedance 2. Of course, one may increase or decrease this degree of resolution to suit any given circumstance by simply adding or subtracting binary stages employed for incrementation.

Referring to FIG. 2, a current normalizer variable impedance for automatic normalization is illustrated as generally comprising a counting register 90 in the lower part of the drawing and a variable impedance 128 in the upper part of the drawing (element 2, FIG. 1).

More specifically, and as will be described in greater detail below, the register 90 comprises a plurality of bistable flipflops $90_1$–$90_n$ which are incremented by a series of trigger pulses received at an input 96. A plurality of gating, monostable and bistable circuits control the operation of the register and a plurality of drivers 116, together with a like plurality of light emitting diodes 120 and light responsive transistors 122 operatively couple the individual stages of the register to corresponding portions of the impedance 128.

It should be noted that the particular embodiment of the invention disclosed herein is unidirectional in the manner in which the variable impedance is varied; that is, the variable impedance 128 is set at a maximum value upon receipt of an initiating signal and is then reduced by the digital varying means including the register 90 until pulses are no longer received. This technique is merely illustrative and not intended to limit the manner in which the variable impedance may be changed. For some applications of the invention, the impedance may be preset to a predetermined value and changed in either direction as the particular application dictates.

As disclosed in the aforementioned Berg patent, the controlling influence which causes the passage of electrolyte through an orifice of an orifice tube is a mercury manometer which includes a start electrode which is contacted by the mercury upon release of a vacuum on the manometer to provide a "start" signal. In the present circuit, this start signal is received at an input 12 in the lower left hand corner of the drawing and is effective at an input 14 of a gate circuit 16 to set a monostable circuit 18, a delaying monostable circuit which functions to abort any "false starts" due to bounce or the like in the start signal caused at the mercury contact. The monostable circuit 18 provides an output pulse of, for example, approximately 20 msec duration, whose trailing edge "clocks" a pair of flip-flops 32 and 34 by way of respective clock inputs 38 and 44, having data inputs 36 and 42 which carry an initiating signal received from the input 12. If the initiating signal is still true at the time of the trailing edge of the output 30 of the monostable circuit 18, both of the flip-flops 32 and 34 will be clocked high causing four things to happen, somewhat simultaneously:

1. The complementary output 48 of the flip flop 34 goes low providing a signal which is inverted by the inverting gate 50 to a high output which develops a signal at the junction between a pair of resistors 52 and 54 for turning on a transistor 56. The transistor 56 provides an output 60 at its collector which is connected to the normalizing relay which has a primary function of bypassing the input amplifier of the associated particle analyzing apparatus and connecting the current normalizer directly to the orifice circuit, as disclosed in the aforementioned Haigh patent;

2. The output 46 of the flip-flop 34 goes high and enables a monostable circuit 66 by way of an input 62 to a gating circuit 64 which causes the monostable circuit to be able to detect the occurrence of null-amplitude when pulses are not received for a predetermined interval, say 20 msec from a gating circuit 82 which receives the trigger pulses at an input 96 from the associated particle analyzing apparatus, the monostable circuit 66 essentially constituting the detector 5 of FIG. 1;

3. The output signal at the output 46 of the flip-flop 34 also enables the trigger gate 82, the gate 82 essentially constituting the entrance point between the detector 5 and the digital impedance variance means 6 of FIG. 1; and 4. The output 40 of the flip-flop 32 goes high and is inverted by a gate 86 (and split and inverted by additional such gates for loading reasons where necessary) to provide a reset signal on a bus 88 for each of the individual stages of the register 90 to reset the impedance value, in this particular embodiment to a maximum value.

An initializing signal is received at an input 92, inverted by a gating circuit 94 and applied to the trigger gate 82. The signal received at the input 92 is overridden when the normalizing relay is pulled in, as noted above and the output of the gate 94 goes high to enable the gate 82 to admit pulses from the trigger, also a part of the detector 5 of FIG. 1, in that it generates pulses when the pulse train from the pulse generator 1 has a higher amplitude than the reference amplitude.

The pulse train rate in this particular embodiment is about 1000/second.

The first trigger pulse received through the gating circuit 82 is applied to the reset input of the flip-flop 32 causing reset of the flip-flop and removal of the reset potential from the register 90. Succeeding pulses then increment the register.

The pulse train at the output of the gate 82 is also applied through the gating circuit 64 to the monostable circuit 66 holding the output 78 thereof high as long as no pulses are missing for longer than 20 milliseconds in the present embodiment.

The output of the gating circuit 100 supplies a voltage which functions as a steady-state digital 1 (true) to those inputs of the register 90 which require such a signal in order that the register be able to perform its counting job. This potential is also applied to the gating circuit 104.

When the monostable circuit 66 fails to detect pulses for 20 msec and its output 78 goes low, the monostable 106 provides a reset pulse by way of its output 114 to reset the flip-flop 34, which in turn causes the normalizing relay circuit to be turned off so that the normalizing relay drops out and the register is set at the null value.

At reset, the simple outputs of the flip-flops $90_1$–$90_n$ are at zero and are all connected to the inputs of respective inverters (drivers) 116, individually referenced $116_1$–$116_n$. The drivers 116 drive light emitting diodes 120, individually referenced $120_1$–$120_n$ by way of corresponding respective resistors $118_1$–$118_n$. The outputs of the drivers are at a predetermined voltage V (for example +5 volts dc) when the inputs of the drivers are at zero. Inasmuch as the other terminals of the light emitting diodes 120 are connected to the potential V, the diodes 120 do not have current flowing therethrough and are in an off condition. Likewise, the associated transistors 122, individually referenced $122_1$–$122_n$, which are optically coupled to the light emitting diodes 120 are off. Therefore, no current flows in the collector resistors of the transistors 122. Also, the collectors and the gates of the FET's are at the same potential as the FET sources and the source potential for the collector resistors. The FET sources and gates are at equal potential and all of the FET's $126_1$–$126_n$ are initially connected in circuit in parallel, the impedance elements being individually referenced $128_1$–$128_n$ and 132. A sample weighting of the impedance values is also illustrated in the drawing ranging from 1.69M down to 374 ohm.

As pulse counting in the register 90 proceeds, the simple outputs of its individual flip-flop circuits $90_1$–$90_n$ go positive as required during counting, turning on the corresponding light emitting diodes 120 and their corresponding transistors, and accordingly turning off the corresponding field effect transistors 126 to remove the corresponding resistive elements from the parallel connected impedance bank 128.

The array of values of the resistors of the impedance bank is such that the reciprocals of the values correspond in relative weighting to the significance of their corresponding register flip-flop circuits in the counting up process of the register. Accordingly, the current which flows through the overall bank of parallel resistors is decremented as each individual pulse is counted on the impedance value register, and each such decrement is equal for each counting pulse.

It should be noted that in the embodiment just described, there is a simple linear relationship between the pulses from the detector (with respect to their number) and the corrective action taken by the digital varying means on the variable impedance in arriving at the null-amplitude condition. It is readily apparent that the speed with which nulling occurs is a matter of the frequency of the pulses and the size of unit change in the impedance (relative to a full-scale value).

The basic concept of converting a particular number of pulses (enter either serially or in parallel) to a particular signal value or to a particular impedance value is behind virtually all digital/analog converters. However, the digital/analog converters are passive transfer devices in the sense that their inputs are fixed at whatever signal is fed in and the resultant output is utilized for what-ever purpose might be at hand.

In the instant invention, however, it should be noted that the output also functions as an operational control for the circuit and has an effect on how many pulses will be emitted, chopping off the pulses entirely when null-amplitude is attained, since the pulses themselves must pass through and be transformed into corresponding pulses of different amplitude in the resistor bank forming the impedance.

Therefore, the present invention has taken advantage of several well known types of circuits and integrated the same in a cooperable relationship to form a system which includes the basic concepts of digital/analog conversion, opto-isolation techniques, a constant amplitude pulse generator, suitable control logic, a reference amplitude level setting circuit and a simple feedback control loop.

As to the optical isolation technique employed between the register 90 and the variable impedance 128, the low voltage circuitry of the register is, of course, protected from the high voltage circuits associated with the variable impedance 128. For example, the voltage V3 may be at −208 volts below system ground with the voltages V1 and V4 at −196 and −230 volts, while the supply potential V is +5 volts dc and the potential V5 is −12 volts dc.

Although the illustrative embodiment of the present invention employs optical isolation, this is merely provided as a nonlimited example in that other isolation techniques could be employed, such as relays. Of course, solid state isolation is preferred in that it gets away from moving parts and deteriorating contacts.

In a particular circuit construction implementing the invention, the bistable circuits were constructed from integrated circuits generally known as 7473 circuits, the transistors 122 and the light emitting diodes 120 from integrated circuits known generally as MOC-1003 circuits, the inverters or drivers from integrated circuits generally known by the number 858, the monostable circuits and associated gates from integrated cicuits generally known by the numbers 7420 and 9601. The diodes employed with the monostable circuits were of the type 1 N 914 and the field effect transistors are of the type 2 N 4859. The bias resistors 130 for the field effect transistors were 50 K, the resistors 124 were 12 M, the resistors 22, 70 and 108 were 10 K, the resistor 52 was 470 ohm and the resistor 54 was 5.6 K. The capacitors 24 and 72 were 6 $\mu$f, the capacitor 110 was 330 pf, and the remainder of the capacitors were 0.01 $\mu$f.

Although I have described my invention by reference to a particular illustrative embodiment, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. A digitally controlled variable impedance comprising:
    a pulse generator for generating a first train of electrical pulses of constant amplitude;
    a variable impedance;
    means for applying the pulse train to said variable impedance to cause generation of a second pulse train corresponding to the first pulse train, variation of the value of said impedance causing a corresponding variance in the amplitude of the pulses of the second pulse train;
    means for setting a reference amplitude value at a detection point;
    digital means operable in response to said first pulse train to vary said impedance; and
    detecting means for detecting matching of the amplitude of said second pulse train with reference amplitude value and causing said digital means to stop varying said variable impedance.

2. The invention set forth in claim 1, wherein said digital means comprises a counting register connected to receive said first pulse train, said register including a plurality of outputs, said impedance comprises a plurality of resistors individually associated with said outputs of said register, and means coupling and electrically isolating said outputs and said resistors and operable in response to pulse count to selectively interconnect said resistors.

3. The invention set forth in claim 2, wherein said coupling and isolating means comprises, for each of said resistors, a light emitting diode connected to a corresponding one of said outputs, a light responsive transistor optically coupled to said light emitting diode and a field effect transistor having a source and a drain connected in series with said resistor and a gate connected to said light responsive transistor.

4. The invention set forth in claim 1, wherein said detecting means comprises a monostable circuit for receiving said first pulse train, said monostable circuit operated to its unstable state by the first pulse received and maintained in that state by each succeeding pulse occurring within a predetermined time interval of the pulse preceding that pulse, said monostable circuit connected to said digital means and operable to cause said digital means to stop varying said impedance when the interval between said pulses becomes greater than said predetermined interval.

5. The invention set forth in claim 1, comprising means for presetting said register to a predetermined count condition including means for receiving a start signal and means for maintaining said register in said predetermined count condition until receipt of a predetermined pulse of the first pulse train.

6. The invention set forth in claim 1, comprising optoisolating means connected between said digital means and said variable impedance and operated by said digital means to vary the value of said variable impedance.

* * * * *